(12) United States Patent
Ota et al.

(10) Patent No.: US 6,679,877 B2
(45) Date of Patent: Jan. 20, 2004

(54) LASER TREATMENT APPARATUS (75) Inventors: Yasuo Ota, Gamagori (JP); Wataru Niwa, Gamagori (JP)

(73) Assignee: Nidek Co., Ltd., Aichi (JP)

( * ) Notice: Subject to any disclaimer, the term of this patent is extended or adjusted under 35 U.S.C. 154(b) by 49 days.

(21) Appl. No.: 09/990,294

(22) Filed: Nov. 23, 2001

(65) Prior Publication Data
US 2002/0068926 A1 Jun. 6, 2002

(30) Foreign Application Priority Data

Dec. 1, 2000 (JP) ........................................ 2000-371489

(51) Int. Cl.⁷ ............................................... A61B 18/18
(52) U.S. Cl. ............................................ 606/9; 606/13
(58) Field of Search ................................ 606/9, 10, 11, 606/13, 16, 17, 18; 351/208, 216, 233; 359/381

(56) References Cited

U.S. PATENT DOCUMENTS 6,384,967 B1 * 5/2002 Watanabe et al. ........... 359/385
6,400,395 B1 * 6/2002 Hoover et al. ................. 348/80
6,436,094 B1 * 8/2002 Reuter ............................ 606/9
6,491,715 B1 * 12/2002 Abels et al. ................... 607/98

FOREIGN PATENT DOCUMENTS

EP  0 880 941 A1  12/1998
EP  1 057 454 A2  12/2000

* cited by examiner

Primary Examiner—Linda C. M. Dvorak
Assistant Examiner—Aaron Roane
(74) Attorney, Agent, or Firm—Oliff & Berridge, PLC (57) ABSTRACT There is disclosed a laser treatment apparatus including: a handpiece internally including an irradiation optical system for irradiating a laser beam for treatment; a lens disposing unit which can dispose a lens in the irradiation optical system, the lens being selectable from among a plurality of lenses of different types having different focal lengths; and a lens detecting unit which detects the type of the lens disposed in the irradiation optical system.

13 Claims, 7 Drawing Sheets

LASER TREATMENT APPARATUS

BACKGROUND OF THE INVENTION

1. Field of the Invention

The present invention relates to a laser treatment apparatus for performing treatment by irradiating a part to be treated with a laser beam for treatment.

2. Description of Related Art

A laser treatment apparatus used in a dermatologic clinic or hospital's dermatoligic department, for example, a laser treatment apparatus for use in depilation or treatment for angioma, is provided with a handpiece in order to irradiate a laser beam for treatment. Some handpieces incorporate a scanning system for scanning a laser beam for treatment on a part to be treated.

Meanwhile, in the apparatus of this type, a spot size of a laser beam for treatment may be changed according to symptoms of portions to be treated and treatment effects. Therefore, plural lens units having condensing lenses for forming different-sized spots are selectively attached to the handpiece.

The apparatus of this type is operated to perform laser irradiation while cooling an irradiation part in order to prevent damages on a skin during the laser irradiation. As a cooling system, there is a system of cooling a window which transmits a treatment laser beam by means of a cooling device and bringing the window into contact with the skin to cool it. This cooling window is also preferably selected from among plural windows different in size according to the size of an irradiation area and the shape of the irradiation part. Therefore there has been proposed an apparatus constructed to selectively attach window units having different-sized windows to the handpiece.

If the lens unit and the window unit are replaced with other units of different types, the type of the new unit has to be input in the apparatus for appropriate operations thereof. In the conventional apparatus, however, such input is manually effected by an operator using switches or the like, which causes the inconvenience of manual operations. If the input is forgotten or an error size is input, laser irradiation conditions such as irradiation density and laser power would be calculated in a different state from a desired one. Thus, proper treatment could not be performed and treatment effect could not be obtained as expected by the operator.

SUMMARY OF THE INVENTION

The present invention has been made in view of the above circumstances and has an object to overcome the above problems and to provide a laser treatment apparatus capable of performing proper treatment by reducing inconvenience of input operations for an operator and preventing human error.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus including: a handpiece internally including an irradiation optical system for irradiating a laser beam for treatment; a lens disposing unit which can dispose a lens in the irradiation optical system, the lens being selectable from among a plurality of lenses of different types having different focal lengths; and a lens detecting unit which detects the type of the lens disposed in the irradiation optical system.

According to another aspect of the present invention, there is provided a laser treatment apparatus including: a handpiece internally including an irradiation optical system for irradiating a laser beam for treatment; a window attaching unit which can attach a window to the handpiece, the window being selectable from among a plurality of windows of different types having different-sized contact surfaces for contact with a skin; a cooling unit which cools the window attached to the handpiece; and a window detecting unit which detects the type of the attached window.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of a preferred embodiment of a laser treatment apparatus embodying the present invention will now be given referring to the accompanying drawings.

Figure 1:
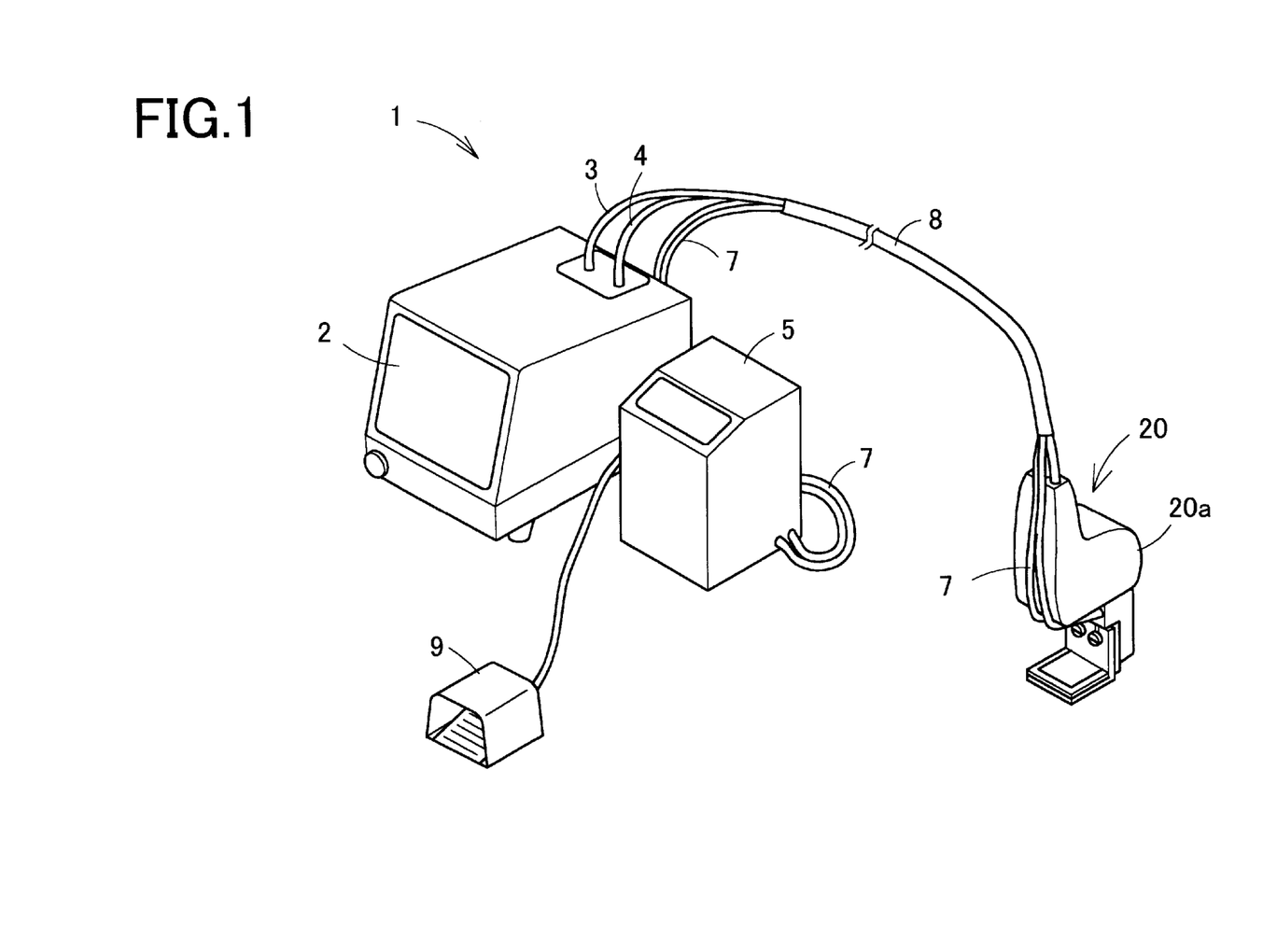
FIG. 1 is a schematic perspective view of a laser treatment apparatus to be used for depilation or other treatments in an embodiment according to the present invention.
Figure 2:
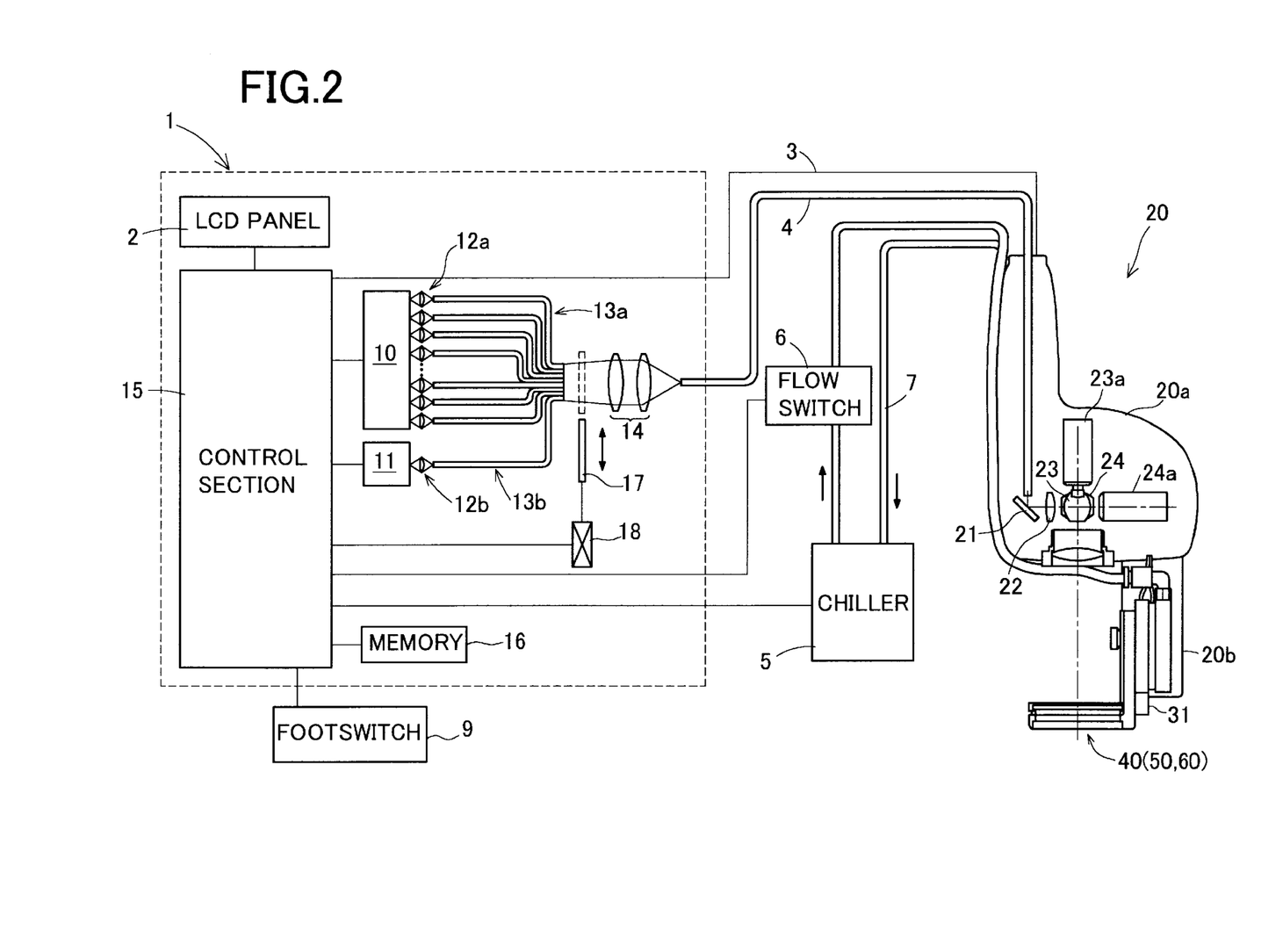
FIG. 2 is a schematic structural view of an optical system and a control system in the apparatus.

FIG. 1 is a schematic perspective view of the laser treatment apparatus to be used in depilation or other treatments in the present embodiment. FIG. 2 is a schematic structural view of an optical system and a control system in the apparatus.

A main unit 1 of the apparatus is provided with a large-sized liquid crystal display (LCD) panel 2 at the front thereof. This LCD panel 2 is made of a touch panel which allows an operator to set various conditions with the touch of corresponding operational keys or buttons appearing on the screen. A communication cable 3 and a fiber cable 4 are provided extending from the top of the main unit 1 to a handpiece 20 for laser irradiation.

Numeral 5 is a chiller for supplying a coolant to the handpiece 20. Two tubes 7 extending from the chiller 5 are tied in a bundle together with the cable 3 and the fiber 4, forming a single concentration cable 8. Numeral 9 is a footswitch for generating a trigger signal to instruct laser irradiation.

In FIG. 2, numeral 10 is a laser source section for emitting laser beams for treatment in pulse form and includes a plurality of laser diodes. The laser beams emitted from the laser diodes are condensed by lenses 12a disposed in correspondence with the laser diodes and become incident on incident end faces of fibers 13a. Exit end face sides of the fibers 13a are tied together in a bundle. The laser beams emitted from the laser diodes are thus combined together at the exit end face sides of the fibers 13a and used as a laser beam with high power for treatment. In the present embodiment, a near infrared light of wavelengths of 800–820 nm is used as a treatment laser beam.

An aiming light beam emitted from an aiming light source 11 is condensed by a condensing lens 12b and made incident on an incident end face of a fiber 13b. An exit end face side of the fiber 13b is tied in a bundle together with the exit end face sides of the fibers 13a. The aiming beam emitted from the fiber 13b is allowed to travel in the same optical path as that of the treatment beam. The aiming beam used in the present embodiment is a red visible light of wavelengths of 620 to 650 nm.

The treatment beam and the aiming beam emitted from the exit end faces of the fibers 13a and 13b tied together are condensed through a group of condensing lenses 14, thus becoming incident on the fiber cable 4. Through this fiber cable 4, which is connected to the handpiece 20, the treatment beam and the aiming beam are delivered to the handpiece 20. As shown in FIG. 2, a shutter 17 is removably disposed on the optical path between the exit end faces of the fibers 13a and 13b and the group of condensing lenses 14 in order to block the beams as needed. The shutter 17 is driven by a driving part 18.

A scanner head 20a of the handpiece 20 is internally provided with a first mirror 23 and a second mirror 24. These first mirror 23 and second mirror 24 are rotated (swung) by a first galvano meter 23a and a second galvano meter 24a respectively, thereby shifting an irradiation position of the treatment beam (the aiming beam) in an X-direction and a Y-direction. Thus, a wide area can be scanned. The beams having delivered into the scanner head 20a through the fiber cable 4 are deflected by a mirror 21 and collimated by a collimator lens 22. Sequentially, the collimated beam is deflected in the X- and Y-directions by the first and second mirrors 23 and 24.

Figure 3:
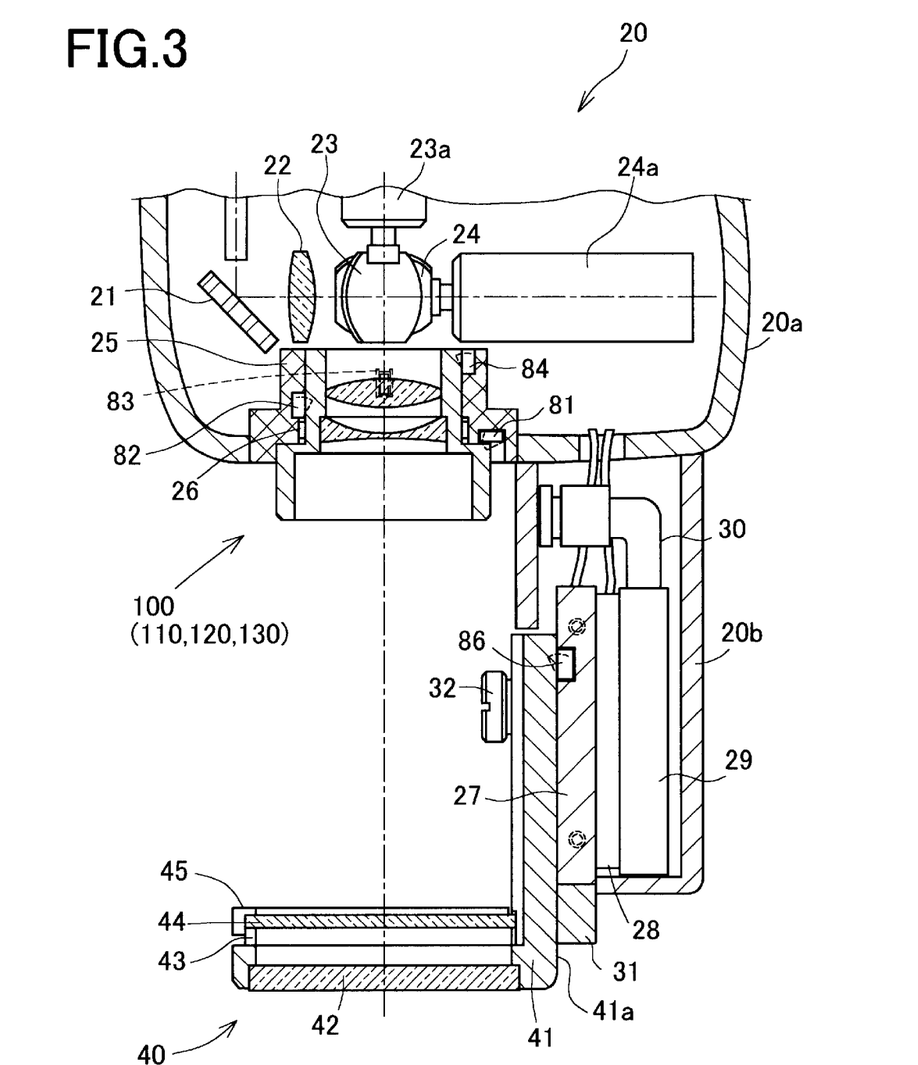
FIG. 3 is an enlarged view showing a schematic structure of a lower part of a handpiece.
Figure 4A:
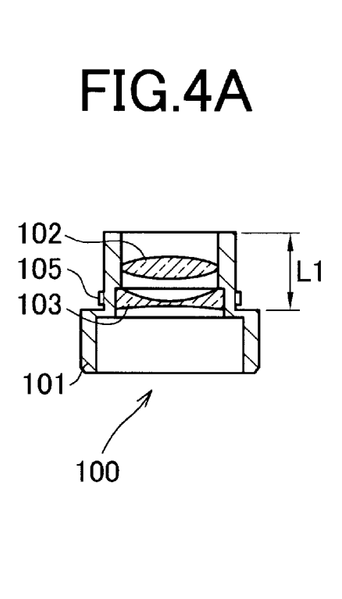
FIGS. 4A to 4D are schematic structural views of lens units for different spot sizes.
Figure 4B:
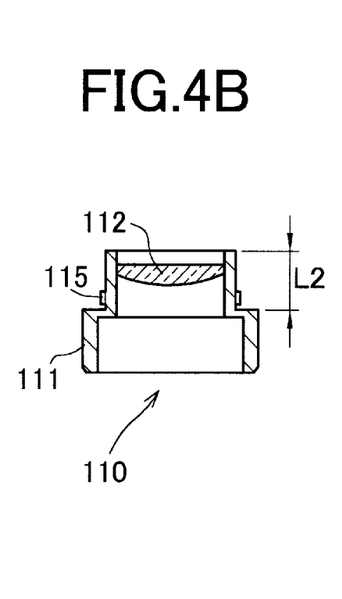
Figure 4C:
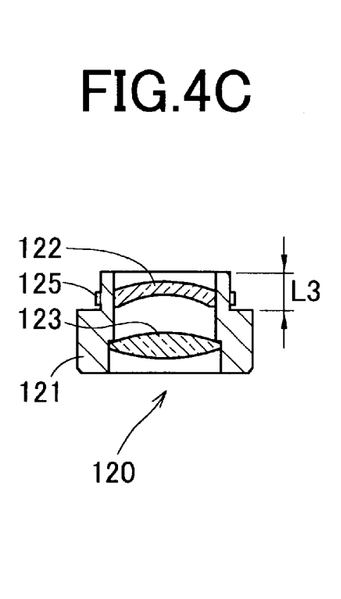
Figure 4D:
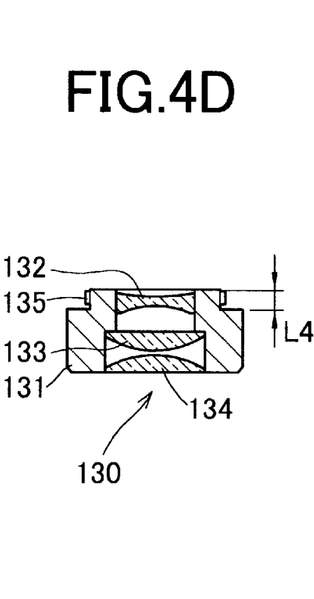

FIG. 3 is an enlarged view of a schematic structure of a lower part of the handpiece 20. A cylindrical mounting part 25 is provided in a laser emission end of the scanner head 20a. This mounting part 25 selectively mounts therein plural types (four types in the present embodiment) of units 100, 110, 120, and 130 (see FIG. 4) having lenses of different focal lengths, thereby forming the treatment beam (the aiming beam) into a spot of various sizes. The inner peripheral surface of the mounting part 25 is formed with a female screw 26, which is engaged with a male screw formed in each of the lens units.

FIGS. 4A to 4D show respective structures of the lens units 100 to 130. In a lens holder 101 of the lens unit 100, a convex lens 102 and a concave lens 103 for condensing the treatment beam into a spot having a size of 5 mm (which is the size on a contact surface of a window unit 40, 50, or 60 mentioned later with a skin) are provided. In a lens holder 111 of the lens unit 110, a convex lens 112 for condensing the treatment beam into a spot having a size of 4 mm is provided. In a lens holder 121 of the lens unit 120, a concave lens 122 and a convex lens 123 for condensing the treatment beam into a spot having a size of 3 mm are provided. In a lens holder 131 of the lens unit 130, a concave lens 132 and two convex lenses 133 and 134 for condensing the treatment beam into a spot having a size of 2 mm are provided. In each of the lens holders, numeral 105, 115, 125, or 135 denotes a male screw part which is engaged with the female screw 26 of the mounting part 25 to screw a corresponding lens holder into the mounting part 25.

Each of the lens holders 101, 111, 121, and 131 is designed to have an upper cylindrical part, which is defined between an upper surface of a flange and an upper end face of the lens holder, having a length L1, L2, L3, or L4 different from one another (L1>L2>L3>L4 in the present embodiment). These upper part lengths L1 to L4 are used as an identifier for identifying the type of a lens holder. As shown in FIG. 3, on the other hand, the mounting part 25 is provided with a lens detecting unit including four switches 81, 82, 83, and 84 for detecting which lens unit is being mounted. The switches 81 to 84 are arranged in this order from below at different heights. The presence or absence of the lens unit in the mounting part 25 is detected by means of the switch 81 which comes into contact with the upper face of the flange of each of the lens holders.

When the lens unit 100 is mounted in the mounting part 25, the switches 82, 83, and 84 are all turned ON according to the upper part length L1 of the lens holder 101. In another case, when the lens unit 110 is mounted in the mounting part 25, the switch 84 remains OFF while the switches 82 and 83 are turned ON because the upper part length L2 of the lens holder 111 is shorter than the length L1. In another case, similarly, when the lens unit 120 is mounted in the mounting part 25, the switches 84 and 83 remain OFF while the switch 82 is turned ON. Furthermore, in another case, when the lens unit 130 is mounted in the mounting part 25, all the switches 84, 83, and 82 remain OFF.

When the switches 81 to 84 are turned ON, corresponding signals are input to a control section 15. In response to the signals representing an ON/OFF state of the switches, the control section 15 detects the type of the lens unit being mounted, namely, the focal length of the mounted lens. Also, the presence or absence of the lens unit in the mounting part 25 can be detected.

In FIG. 3, a scanner base 20b made of polyacetal resin having an excellent heat insulation property is fixed on the underside of the scanner head 20a. In this scanner base 20b, a window attaching plate 27 made of aluminum having good thermal conductivity is secured with screws from side (in a perpendicular direction to the drawing paper of FIG. 3). Numeral 28 is a Peltier device used as an electronic heat exchanger. This Peltier device 28 is mounted in sandwich relation between a cooling plate 29 made of aluminum and the attaching plate 27. An electric current is fed through the Peltier device 28 so that its one surface in contact with the attaching plate 27 serves as a heat-absorbing side (a cooling side) and the other surface in contact with the cooling plate 29 serves as a heat-radiating side. The cooling plate 29 is internally provided with a passage for circulating a coolant. The coolant cooled in the chiller 5 is delivered through the tube 7 and a pipe 30 to the cooling plate 29 and circulated therein, which absorbs the heat radiated from the Peltier device 28 through the cooling plate 29.

Numeral 31 is a temperature sensor attached to a lower end of the attaching plate 27. This temperature sensor 31 detects the temperature of the plate 27. Based on the detected temperature, the control section 15 controls the temperature of the Peltier device 28.

A window unit to be attached to the attaching plate 27 is replaceable and freely selected from among plural window units; namely, a LARGE window unit 40, a MEDIUM window unit 50, and a SMALL window unit 60, which have different-sized surfaces for contact with a skin.

FIG. 3 shows the LARGE window unit 40 having a contact surface of a largest size (40 mm×40 mm) among the window units. This window unit 40 is structured of: a first window 42 that is made of transparent sapphire glass having good heat conductivity and can be brought into contact with a skin; a window frame 41 of a substantial L-shape in a side view for holding the first window 42; a heat insulating plate 43 in frame form, made of polyacetal resin having an excellent heat insulation property; a second window 44 made of transparent glass which is inferior in heat conductivity to the first window 42; and a cover 45 made of aluminum with an opening. This arrangement allows the heat of the first window 42 to be transmitted to the window frame 41, the window attaching plate 27, and the Peltier device 28 in turn, and absorbed by the coolant through the cooling plate 29. Thus, decreasing the temperature of the first window 42 can cool the skin of a patient. Moreover, the temperature of the second window 44 is close to a room temperature, so that no condensation occurs on the surface of the second window 44.

When the operator attaches the LARGE window unit 40 to the lower part of the scanner head 20a and then brings the first window 42 into contact with the skin of a patient, the part to be treated (treatment part) can be uniformly flattened and the scanner head 20a can be held stably. The window units are designed to have an appropriate distance between the condensing lenses of each of the lens units and the lower surface of the first window 42 so that the treatment beam emitted from the scanner head 20a is condensed on a position near the lower surface of the first window 42.

Figure 5:
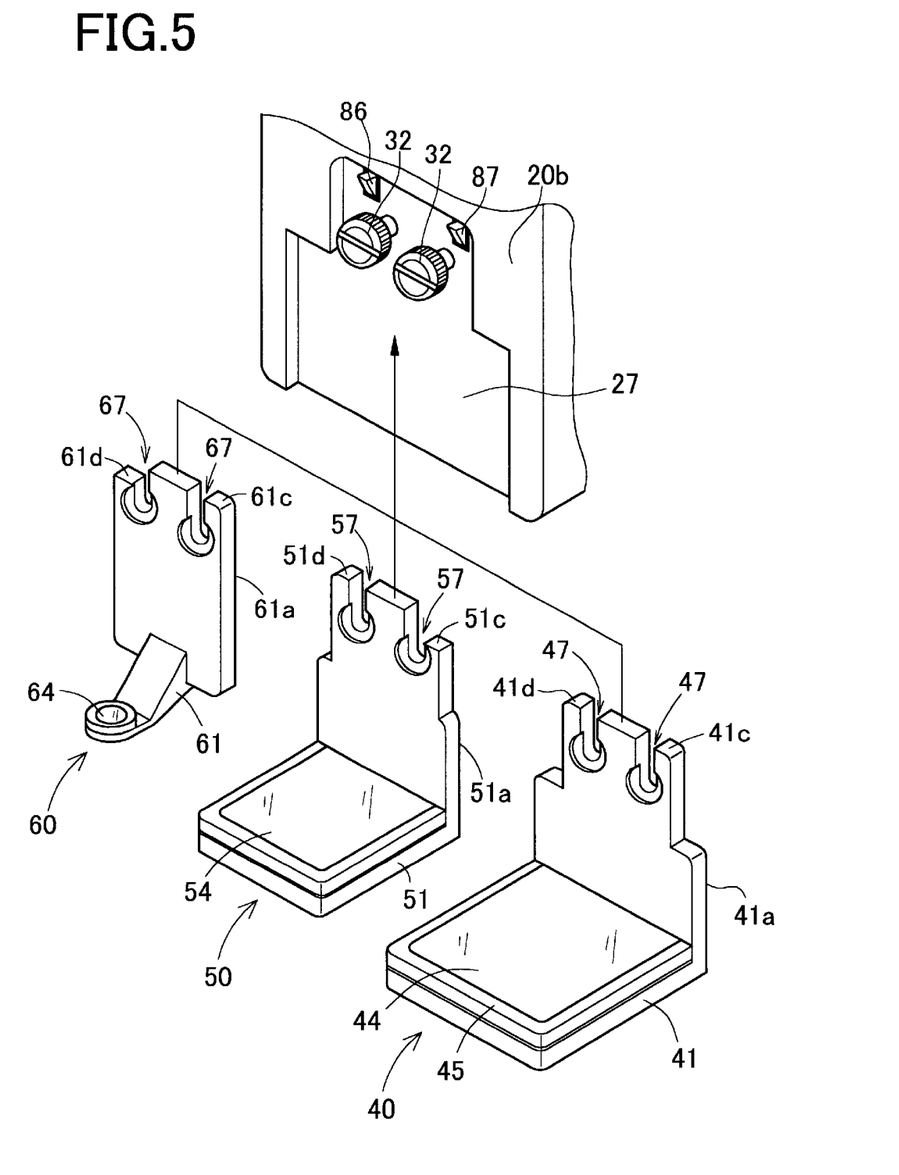
FIG. 5 is an explanatory view showing window units of different sizes and shapes and a method of replacing the units.

FIG. 5 also shows the MEDIUM window unit 50 with a contact surface of a medium size (30 mm×30 mm) and the SMALL window unit 60 with a contact surface of a small size (a circle of 10 mm in diameter). As with the LARGE window unit 40, the MEDIUM window unit 50 has a first window for contact with a skin under a second window 54 and the SMALL window unit 60 has a first window for contact with a skin under a second window 64. These units 50 and 60 are different from the unit 40 only in size and shape of the windows, but similar to the same in basic structure. The detailed explanations thereof are therefore omitted.

Next, mounting structures of the window units 40, 50, and 60 and a system for detecting the types of the window units are explained with reference to FIG. 3 and FIG. 5.

In the LARGE window unit 40, the frame 41 is provided with a back plate 41a including an upper portion formed with two U-shaped slots 47. This window unit 40 is detachable/attachable with respect to the attaching plate 27 by means of two screws 32. Similarly, the frame 51 of the MEDIUM window unit 50 is provided with a back plate 51a including an upper portion formed with two U-shaped slots 57, and the frame 61 of the SMALL window unit 60 is provided with a back plate 61a including an upper portion formed with two U-shaped slots 67. Those window units 50 and 60 are also detachable/attachable with respect to the attaching plate 27 with the two screws 32.

In the attaching plate 27, a window detecting unit including switches 86 and 87 is provided for detection of the size of a window attached to the attaching plate 27. Accordingly, the window units 40, 50, and 60 are different in shape of the portions for attachment (the upper portions of the back plates).

The back plate 61a of the SMALL window unit 60 is formed with a left shoulder portion 61d shorter in length (height) than a right shoulder portion 61c, so that the switch 86 remains OFF while the switch 87 is turned ON when this unit 60 is attached to the attaching plate 27. The back plate 51a of the MEDIUM window unit 50 is formed with a right shoulder portion 51c shorter in length than a left shoulder portion 51d, so that the switch 86 is turned ON while the switch 87 remains OFF when this window unit 50 is attached to the attaching plate 27. The back plate 41a of the LARGE window unit 40 is provided with a right shoulder portion 41c and a left shoulder portion 41d which have the same long length, so that both the switches 86 and 87 are turned ON when this window unit 40 is attached to the attaching plate 27. In this way, the different shoulder portions among the window units are used as identifiers to identify the window unit being mounted. The control section 15 receives a signal representative of a combination of ON and OFF states of the switches 86 and 87, and determines which window unit is being mounted. As mentioned above, when any one of the window units is attached to the attaching plate 27, at least one of the switches 86 and 87 is turned ON. Accordingly, the presence or absence of the window unit on the window attaching plate 27 can be checked at the same time.

The control section 15 shown in FIG. 2 is connected to the LCD panel 2, the chiller 5, a flow switch 6 used to monitor whether the coolant from the chiller 5 normally circulates, a memory 16, and the footswitch 9. The temperature sensor 31 provided on the handpiece 20 side, the first galvano meter 23a, the second galvano meter 24a, and the Peltier device 28 are connected to the control section 15 via the communication cable 3.

Operations of the laser treatment apparatus having the above mentioned structure are explained below.

An operator selects a lens unit for a desired spot size from among the lens units 100, 110, 120, and 130 according to the position of a part to be irradiated (an irradiation part), or a part to be treated (a treatment part), and its size, and mounts the selected one in the mounting part 25 of the handpiece 20. The operator also selects a window unit of an appropriate window size from among the units 40, 50, and 60 and attaches the selected unit to the attaching plate 27. For example, if the treatment part is flat and large, the LARGE window unit 40 is used in order to make efficient laser irradiation over a wide area by scanning. If the treatment part is relatively small, the MEDIUM window unit 50 is used to reduce the contact area of the window with the skin outside the treatment part, thereby preventing the skin outside the irradiation part from being cooled and reducing a burden on the patient. If the treatment part is in a portion of indefinite shape such as a face, an armpit, and an abdomen, instead of the LARGE window unit 40, the MEDIUM window unit 50 or the SMALL window unit 60 is preferably used, which can provide a good operability and also be handled easily even to a small treatment part. With respect to a fine treatment part or a considerably uneven portion such as a nose, a mouth, the surrounding of an eye, the SMALL window unit 60 is preferably used to allow laser irradiation and cooling and to improve the operability to the operator.

In the following description, explanation is made assuming that the lens unit 100 for a spot size of 5 mm and the LARGE window unit 40 are attached to the handpiece 20.

When the lens unit 100 is attached, signals representing that the switches 81 to 84 are all turned ON are transmitted to the control section 15. This control section 15 then determines that the spot size is 5 mm. When the LARGE window unit 40 is mounted, sequentially, signals representing that both the switches 86 and 87 are turned ON are transmitted to the control section 15. The control section 15 judges that the size of the window unit mounted is LARGE. The information about the spot size is displayed in a display part 200 on the display screen of the LCD panel 2 in FIG. 6. The information that the LARGE window unit 40 is being mounted is displayed in a display part 201.

Figure 6:
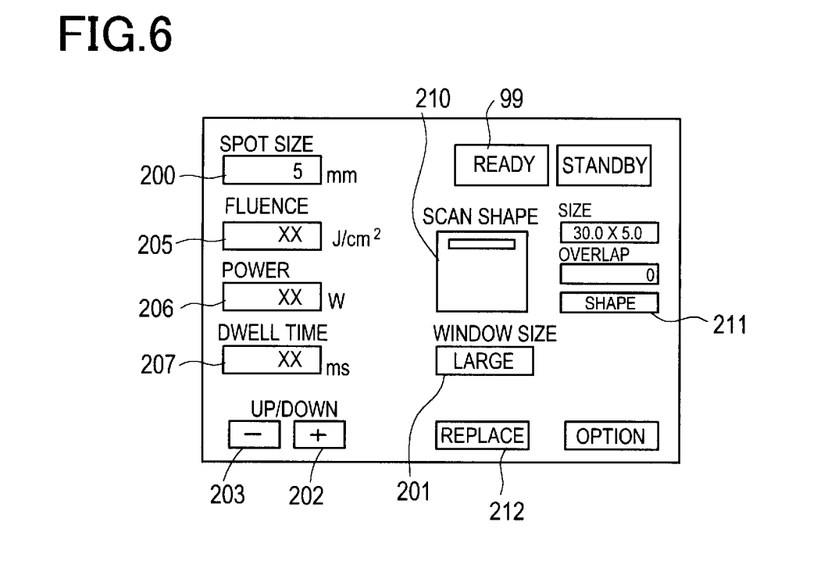
FIG. 6 is a view of a display screen of an LCD panel.

The operator operates the setting keys or buttons appearing on the LCD panel 2 to set other irradiation conditions. To input each numeric value, the operator pushes an UP button 202 or a DOWN button 203 to increase or decrease the numeral displayed in each display part. The irradiation density is set in a FLUENCE display part 205, the laser power is set in a display part 206, and the pulse time is set in a display part 207. At this time, when two of the three irradiation conditions are set, the rest is calculated by the control section 15 in relation to a spot size automatically detected. During laser irradiation, the laser light source 10 is controlled to operate in accordance with the set irradiation conditions.

Figure 7:
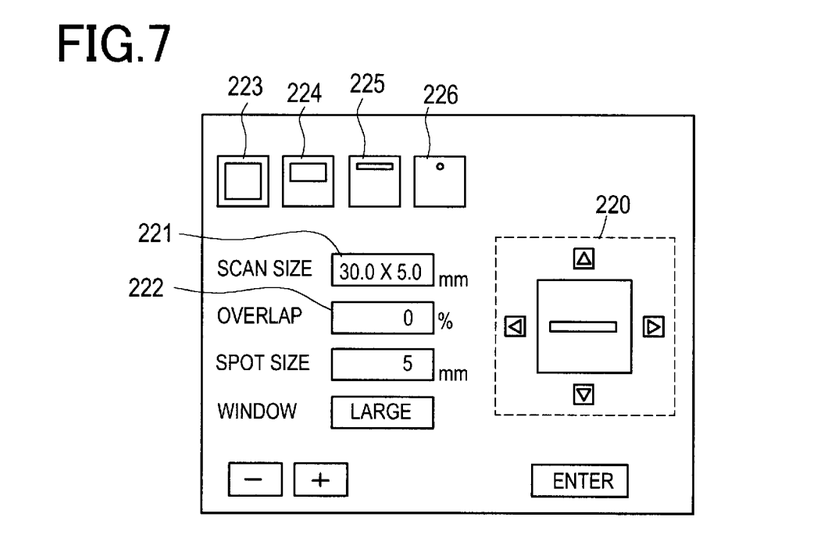
FIG. 7 is a view of a scanning setting screen.
Figure 8:
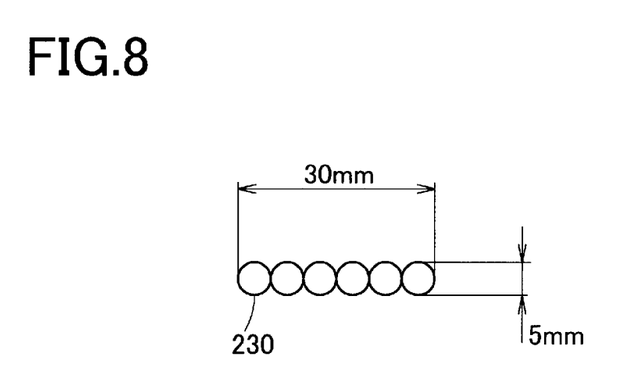
FIG. 8 is an explanatory view to determine spot positions in a scanning operation.

The shape of a scanning pattern is displayed in a display part 210. With press of a button 211, the screen is switched to a scanning setting screen shown in FIG. 7 for allowing a change of scanning pattern shapes. The scanning pattern shape can be selected from among plural patterns previously stored in the memory 16. In the present embodiment, a square pattern 223, a rectangular pattern 224, a linear pattern 225, and a non-scanning pattern 226 are prepared. On the scanning setting screen, four directional buttons provided within a display region 220 are used to change the size of a scanning area (which is displayed in a display part 221). At this time, the maximum value of the scanning area size allowed to be input is restricted based on the detected result on the type (size) of the window unit. On the other hand, the minimum value of the scanning area size allowed to be input is restricted based on the detected result on the type of the lens unit. The degree of overlap of spots can be set in a display part 222. Based on this value and the scanning area size set in the display region 220, spot positions during scanning are calculated. For example, in the setting condition that the overlapping degree of spots is 0% and the scanning area size is 30 mm×5 mm, positions of six spots 230 (i.e., intervals between spots, each interval corresponding to a set value of a mirror swinging angle per spot) are determined as shown in FIG. 8. During laser irradiation, the first and second galvano meters 23a and 24a are controlled to operate in accordance of the thus set conditions.

After preparations on the main unit 1 side, the operator holds the handpiece 20 by hand to bring the first window 42 into contact with the treatment part. The aiming beam emitted from the light source 11 is irradiated from the scanner head 20a and made to repeatedly scan the area corresponding to the selected scanning pattern shape by driving of the first and second galvano meters 23a and 24a. The operator adjusts the contact position of the first window 42 while observing the treatment part and the irradiating position of the aiming beam through the windows 42 and 44.

After completion of alignment of the irradiation part by observation of the aiming beam and setting of the laser power and other conditions, the operator pushes the switch 99 to place the apparatus in a READY state. When a trigger signal from the footswitch 9 is input, the control section 15 controls driving of the first and second galvano meters 23a and 24a to scan the treatment beam to irradiate the treatment part in the selected scanning area.

During the laser irradiation, the cooling system is activated with an unillustrated switch. More specifically, the Peltier device 28 and the chiller 5 are driven to cool the first window 42, thus cooling the treatment part in contact with the first window 42.

Changing the spot size during the operation is carried out in the following manner. The operator first pushes a REPLACE button 212 on the LCD panel 2. Upon push of the button 212, the control section 15 inserts the shutter 17 into the optical path to prevent the treatment beam from being irradiated accidentally. The operator demounts the previously-mounted lens unit 100 for the spot size of 5 mm in diameter and, instead thereof, attaches another lens unit for a desired spot size, for example, the lens unit 120 for a spot size of 3 mm in diameter. When the lens holder 121 is fully screwed in the mounting part 25, signals representing that the switches 81 and 82 are ON and the switches 83 and 84 are OFF are transmitted to the control section 15, which then determines that the current lens holder is for a spot size of 3 mm in diameter. The control section 15 causes the spot size display part 200 on the LCD panel 2 to display that the spot size is 3 mm in diameter. According to the change in the spot size, the control section 15 recalculates the laser irradiation conditions. The control section 15 is programmed to alter the irradiation density in the display part 205 when the spot size is changed during the operation. Alternatively, it may be programmed to change the pulse time or the laser power to maintain the energy density as set before the spot size is changed. In this case, which condition is used may be previously selected.

In association with the change of spot sizes, the set value of the swinging angle per spot of each of the first and the second galvano meters 23a and 24a is changed. After completion of replacement of the lens units, the operator pushes the button 212 again. Thus, the shutter 17 is moved out of the optical path, placing the apparatus in a laser irradiation enabled state.

Replacing the window unit during the operation is effected with push of the REPLACE button 212 in the same manner as above. The operator detaches the previously-attached LARGE window unit 40 from the handpiece 20, and then attaches another window unit of a desired size. If the MEDIUM window unit 50 is attached, for example, signals representing that the switch 87 is OFF and the switch 86 is ON are transmitted to the control section 15, which determines that the size of the window unit currently attached is MEDIUM. The control section 15 causes the display part 201 on the LCD panel 2 to display that the size of the window unit is MEDIUM.

According to the change of window units, the control section 15 displays a message to request the operator to input again the scanning area size if the previously-set scanning area size exceeds the size of the current window unit. The value of the scanning area size allowed to be input is restricted within the window size currently attached. In other words, if a scanning area size exceeding the window unit size is input, the control section 15 does not accept the input. Upon completion of the proper input, the control section 15 changes the swinging angles of the first and second galvano meters 23a and 24a to irradiate the treatment beam within the frame of the changed window unit.

In association with the change of window units, the control of cooling the unit is also changed. A set voltage and an ON/OFF time of the voltage for driving the cooling device (Peltier device 28 and chiller 5) which cools the window unit are generally determined according to the window unit size. The control section 15 therefore reads data on a driving manner of the cooling device suitable for the window unit size from the memory 16 and cools the window unit in the driving manner upon change of the window units. Accordingly, the window unit can be cooled close to the set cooling temperature faster than the method of controlling the temperature only by the temperature sensor 31.

In the above description, the types of the lens units and the window units are identified or detected based on mechanical ON/OFF states of the switches for detection. This arrangement may be variously altered; for example, marks of various kinds which can optically be read are applied to the units to identify the types thereof.

As described above, according to the present invention, operations needed to input a spot size or a window unit size can be reduced. Furthermore, the present invention can prevent human errors from occurring when lenses for different spot sizes or windows of different sizes are replaced, so that appropriate treatment can be effected.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus, including:
   a handpiece internally including an irradiation optical system for irradiating a laser beam for treatment;
   a lens mounting unit to mount a lens in the irradiation optical system, the lens being selectable from among a plurality of lenses of different types having different focal lengths; and
   a lens detecting unit which detects the type of the lens mounted in the irradiation optical system.

2. The laser treatment apparatus according to claim 1, wherein the lens mounting unit mounts a lens unit having the lens in a laser beam emission end of the handpiece, the lens unit being selectable from among a plurality of lens units provided with the lenses of different types.

3. The laser treatment apparatus according to claim 2, wherein the lens detecting unit is provided in the lens mounting unit and detects the type of the lens unit.

4. The laser treatment apparatus according to claim 1, further including an irradiation condition determining unit which determines conditions for laser irradiation based on a detection result by the lens detecting unit.

5. The laser treatment apparatus according to claim 4, further including an irradiation condition setting unit which sets the laser irradiation conditions including irradiation density, power, and pulse time of the laser beam, wherein when a certain condition of the laser irradiation conditions is set, the irradiation conditions determining unit automatically determines other conditions.

6. The laser treatment apparatus according to claim 1, further including a display unit which displays a detection result by the lens detecting unit.

7. The laser treatment apparatus according to claim 1, further including:
   a scanning unit disposed in the irradiation optical system and used for scanning the laser beam; and
   a scanning control unit which controls driving of the scanning unit based on a detection result by the lens detecting unit.

8. A laser treatment apparatus including:
   a handpiece internally including an irradiation optical system for irradiating a lser beam for treatment;
   a window attaching unit which can attach a window to the handpiece, the window being selectable from among a plurality of windows of different types having different-sized contact surfaces for contact with a skin;
   a cooling unit which cools the window attached to the handpiece; and
   a window detecting unit which detects the type of the attached window.

9. The laser treatment apparatus according to claim 8, wherein the window detecting unit is provided in the window attaching unit and detects types of different window units provided with the windows of different types.

10. The laser treatment apparatus according to claim 8, further including a display unit which displays a detection result by the window detecting unit.

11. The laser treatment apparatus according to claim 8, further including:
    a scanning unit disposed in the irradiation optical system and used for scanning the laser beam; and
    a scanning control unit which controls driving of the scanning unit based on a detection result by the window detecting unit.

12. The laser treatment appratus according to claim 8, further including:
    a scanning unit disposed in the irradiation optical system and used for scanning the laser beam; and
    an input unit which inputs a scanning area to be scanned by the scanning unit, the scanning area allowed to be input being restricted based on a detection result by the window detecting unit.

13. The laser treatment apparatus according to claim 8, further including a cooling control unit which controls driving of the cooling unit based on a detection result by the window detecting unit.

* * * * *